US008661927B2

(12) United States Patent
Anderson et al.

(10) Patent No.: US 8,661,927 B2
(45) Date of Patent: Mar. 4, 2014

(54) CABLE RE-ORDERING DEVICE

(75) Inventors: S. Christopher Anderson, San Francisco, CA (US); Thomas G. Cooper, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 322 days.

(21) Appl. No.: 12/780,747

(22) Filed: May 14, 2010

(65) Prior Publication Data

US 2011/0277579 A1    Nov. 17, 2011

(51) Int. Cl.
*B25J 18/00* (2006.01)

(52) U.S. Cl.
USPC .............. 74/490.04; 901/21; 600/101; 600/1

(58) Field of Classification Search
USPC ................... 74/490.04, 502.4, 502.6; 901/21; 248/56–61, 65, 68; 174/56–61, 65, 174/68.127, 100
See application file for complete search history.

(56) References Cited

U.S. PATENT DOCUMENTS

| 422,373 | A | * | 3/1890 | Caldwell | 56/332 |
|---|---|---|---|---|---|
| 2,421,279 | A | * | 5/1947 | Marty | 446/331 |
| 2,765,930 | A | * | 10/1956 | Greer et al. | 414/7 |
| 3,091,890 | A | * | 6/1963 | Allen | 446/338 |
| 3,369,427 | A | * | 2/1968 | Brighton et al. | 74/502.1 |
| 4,007,646 | A | * | 2/1977 | De Jonge | 74/501.6 |
| 4,751,821 | A | * | 6/1988 | Birchard | 60/698 |
| 4,834,761 | A | * | 5/1989 | Walters | 623/26 |
| 5,297,443 | A | * | 3/1994 | Wentz | 74/490.04 |
| 5,306,199 | A | * | 4/1994 | Locricchio | 446/177 |
| 5,325,845 | A | * | 7/1994 | Adair | 600/114 |
| 5,599,151 | A | * | 2/1997 | Daum et al. | 414/7 |
| 5,618,294 | A | * | 4/1997 | Aust et al. | 606/170 |
| 5,807,376 | A | * | 9/1998 | Viola et al. | 606/1 |
| 5,880,402 | A | * | 3/1999 | Nugent | 174/27 |
| 7,543,518 | B2 | * | 6/2009 | Buckingham et al. | 74/490.05 |
| 7,553,275 | B2 | * | 6/2009 | Padget et al. | 600/142 |
| 7,744,608 | B2 | * | 6/2010 | Lee et al. | 606/130 |
| 8,105,350 | B2 | * | 1/2012 | Lee et al. | 606/205 |
| 8,205,522 | B2 | * | 6/2012 | Buckingham et al. | 74/490.04 |
| 2003/0135204 | A1 | * | 7/2003 | Lee et al. | 606/1 |
| 2004/0193146 | A1 | * | 9/2004 | Lee et al. | 606/1 |
| 2006/0095074 | A1 | | 5/2006 | Lee et al. | |
| 2006/0111615 | A1 | | 5/2006 | Danitz et al. | |
| 2008/0221391 | A1 | * | 9/2008 | Weitzner et al. | 600/118 |
| 2008/0261483 | A1 | * | 10/2008 | Rugolo et al. | 446/334 |
| 2009/0095112 | A1 | * | 4/2009 | Buckingham et al. | 74/490.05 |
| 2009/0143647 | A1 | * | 6/2009 | Banju | 600/149 |
| 2012/0205153 | A1 | * | 8/2012 | Larson et al. | 174/88 S |

* cited by examiner

*Primary Examiner* — Troy Chambers
*Assistant Examiner* — Valentin Craciun

(57) ABSTRACT

A cable guide re-orders a plurality of cables. A first guide plate has a plurality of first guide holes that receive a plurality of cables in a first order. A second guide plate has a plurality of second guide holes that receive the plurality of cables in a different second order. An intermediate guide plate is located between the first and second guide plates. The intermediate guide plate has a plurality of intermediate guide holes. Each of the intermediate guide holes receives one of the plurality of cables and causes a change of direction in the cable to facilitate the change from the first to the second order. The intermediate guide plate may further include cable passages to allow some cables to pass through without changing direction. There may be more than one intermediate guide plate. The cables may change from a generally linear to a generally circular arrangement.

24 Claims, 6 Drawing Sheets

CABLE RE-ORDERING DEVICE

BACKGROUND

1. Field

Embodiments of the invention relate to the field of cable guides; and more specifically, to devices which contact a plurality of cables moving relative to the device, and change the order of the cables for transmitting forces to surgical instruments intended for use in minimally invasive surgeries.

2. Background

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

The elongated surgical instruments will generally have an end effector in the form of a surgical tool such as a forceps, a scissors, a clamp, a needle grasper, or the like at one end of an elongate tube. The surgical tool is generally coupled to the elongate tube by one or more articulated sections to control the position and/or orientation of the surgical tool. An actuator that provides the actuating forces to control the articulated section is coupled to the other end of the elongate tube. A means of coupling the actuator forces to the articulated section runs through the elongate tube. Two actuators may be provided to control two articulated sections, such as an "arm" that positions the surgical tool and a "wrist" the orients and manipulates the surgical tool, with means for coupling both actuator forces running through the elongate tube.

Cables may be used as the means of coupling the actuator forces to the articulated sections because of the flexibility they provide and because of the ability of a cable to transmit a significant force, a substantial distance, through a small cross-section. The actuators may be relatively bulky and it may be difficult to arrange the actuators to couple the applied forces to the cables in the arrangement needed for the cables within the elongate tube. The transition from the arrangement of the cables at the attachment to the actuators to the arrangement at the end of the elongate tube may require the cables to cross over one another to re-order the adjacency of the cables.

In view of the above, it is desirable to provide an apparatus and method for guiding a plurality of cables between actuators and an elongate tube of a surgical instrument intended for use in minimally invasive surgeries that re-orders the adjacency of the cables in a compact and efficient manner.

SUMMARY

A cable guide re-orders a plurality of cables. A first guide plate has a plurality of first guide holes that receive a plurality of cables in a first order. A second guide plate has a plurality of second guide holes that receive the plurality of cables in a different second order. An intermediate guide plate is located between the first and second guide plates. The intermediate guide plate has a plurality of intermediate guide holes. Each of the intermediate guide holes receives one of the plurality of cables and causes a change of direction in the cable to facilitate the change from the first to the second order. The intermediate guide plate may further include cable passages to allow some cables to pass through without changing direction. There may be more than one intermediate guide plate. There may be a center tube that supports the plates and may further guide some cables in a change of direction. The cables may change from a generally linear to a generally circular arrangement.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
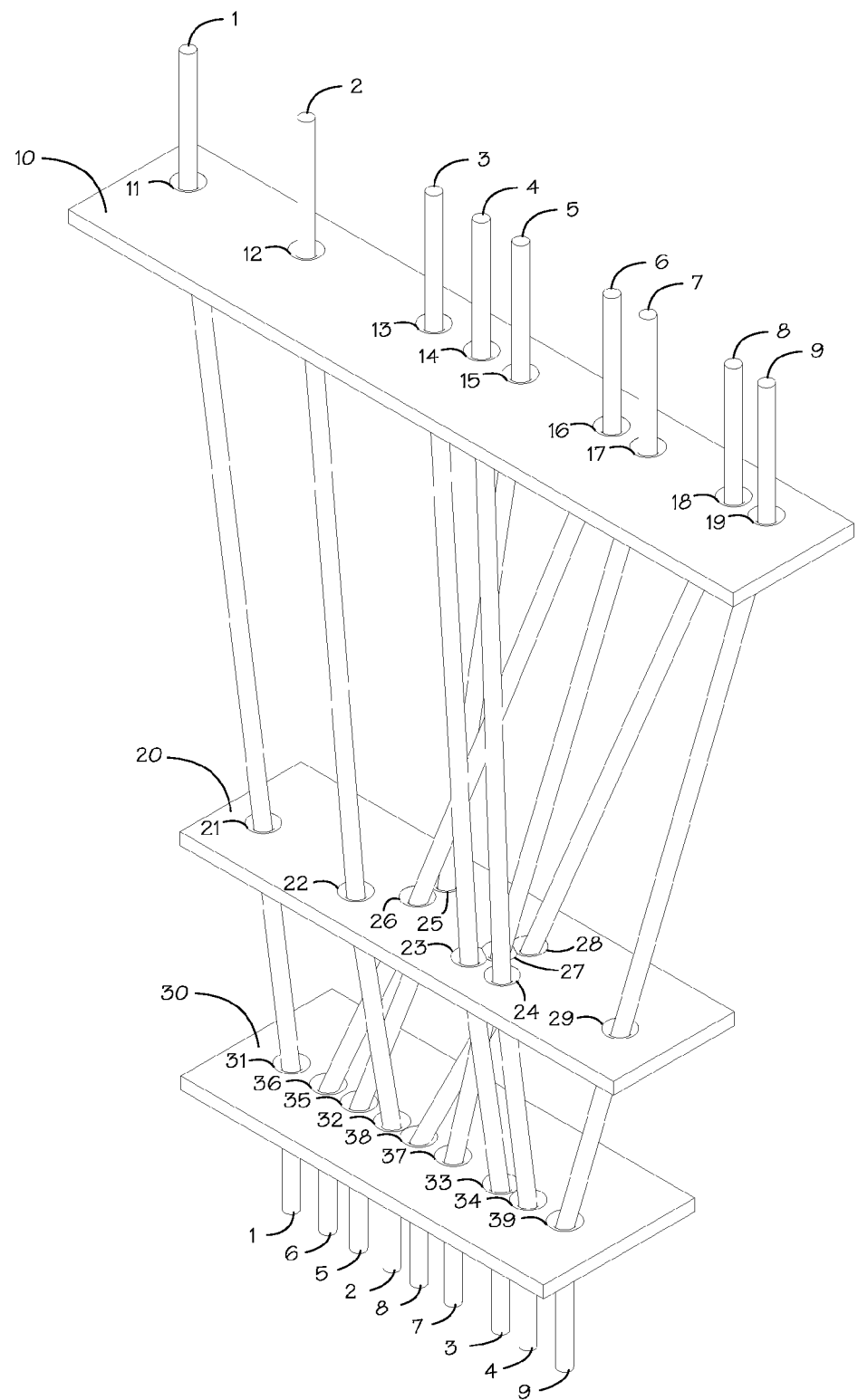
FIG. 1 is a perspective view of a cable guide that re-orders a plurality of cables.

FIG. 1 is a perspective view of a cable guide that re-orders a plurality of cables 1-9, in accordance with embodiments of the present invention.

A first guide plate 10 has a plurality of first guide holes 11-19 that receive a plurality of cables 1-9 in a first order. A second guide plate 30 has a plurality of second guide holes 31-39 that receive the plurality of cables 1-9 in a different second order. An intermediate guide plate 20 is located between the first 10 and second 30 guide plates. The intermediate guide plate 20 has a plurality of intermediate guide holes 22-28. Each of the intermediate guide holes 22-28 receives one 2-8 of the plurality of cables and causes a change of direction in the cable to facilitate the change from the first to the second order. In the embodiment illustrated, the intermediate guide plate 20 further includes cable passages 21, 29 to allow some cables 1, 9 to pass through the intermediate guide plate without changing direction.

The intermediate guide holes are located on the intermediate guide plate to route the cables so that they will not rub against one another. The intermediate guide plate is preferably constructed of materials and configuration that minimizes the friction between the cables and the guide plate. The use of the cable guide can be advantageous when it is desirable to arrange the cables in a first order that is advantageous based on the construction of an actuator that drives the cables and then rearrange the cables to a second order that is advantageous for driving a device with the cables.

Figure 2:
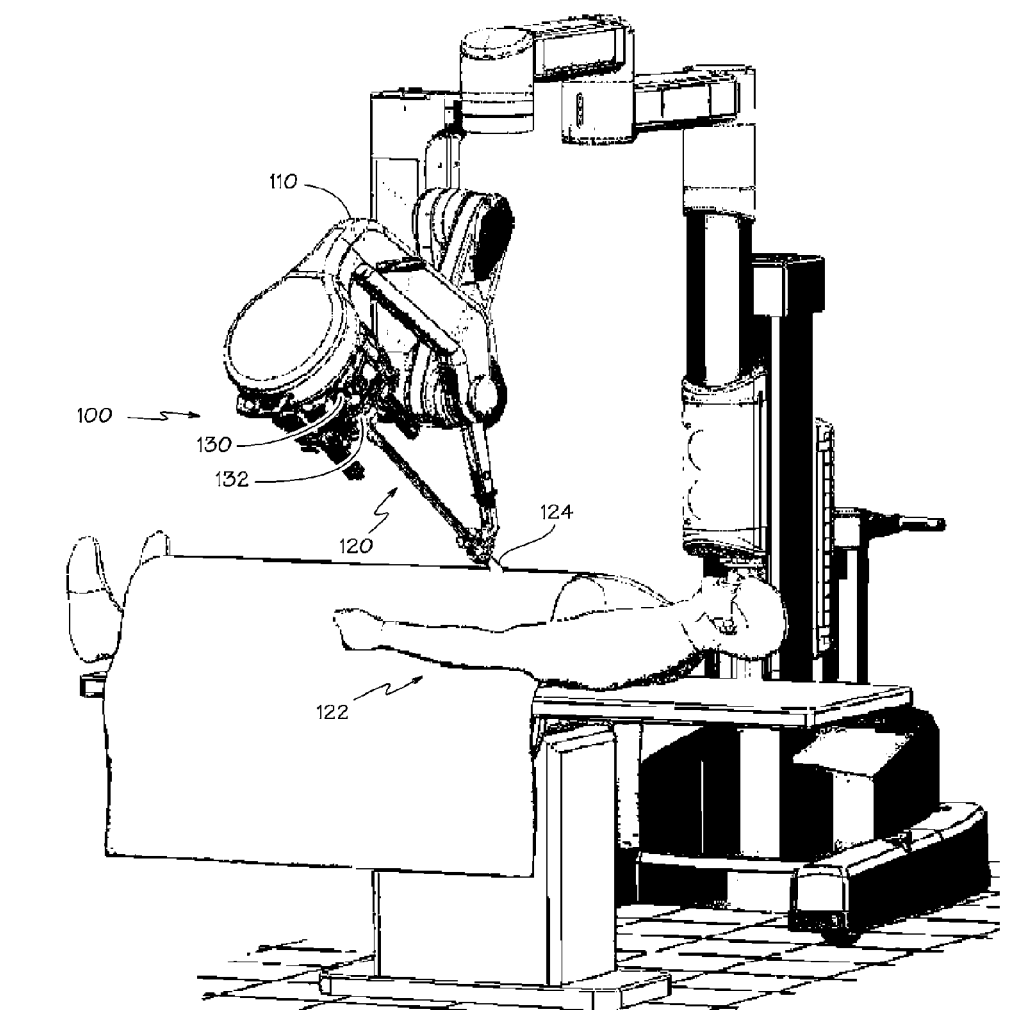
FIG. 2 is a simplified perspective view of a robotic surgical system with a robotically controlled surgical instrument inserted through a port in a patient's abdomen.

FIG. 2 is a simplified diagrammatic perspective view of a robotic surgical system 100, in which the present invention can be used. The system 100 includes a support assembly 110 mounted to or near an operating table supporting a patient's body 122. The support assembly 110 supports one or more surgical instruments 120 that operate on a surgical site within the patient's body 122.

The term "instrument" is used herein to describe a device configured to be inserted into a patient's body and used to carry out surgical procedures. The instrument includes a surgical tool, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support for the surgical tool so that the position and orientation of the surgical tool can be manipulated.

The simplified perspective view of the system 100 shows only a single instrument 120 to allow aspects of the system to be more clearly seen. A functional robotic surgical system would further include a vision system that enables the operator to view the surgical site from outside the patient's body 122. The vision system can include a video monitor for displaying images received by an optical device provided at a distal end of one of the surgical instruments 120. The optical device can include a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, marketed by Intuitive Surgical, Inc., of Sunnyvale Calif.

A functional robotic surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control servo motors which, in turn, control the articulation of the surgical assembly. The forces generated by the servo motors are transferred via drivetrain mechanisms, which transmit the forces from the servo motors generated outside the patient's body 122 through an intermediate portion of the elongate surgical instrument 120 to a portion of the surgical instrument inside the patient's body 122 distal from the servo motor. Persons familiar with telemanipulative, teleoperative, and telepresence surgery will know of systems such as the da Vinci® Surgical System and the Zeus® system originally manufactured by Computer Motion, Inc. and various illustrative components of such systems.

The surgical instrument 120 is shown inserted through an entry guide 124, e.g., a cannula in the patient's abdomen. A functional robotic surgical system may provide an entry guide manipulator (not shown; in one illustrative aspect the entry guide manipulator is part of the support system 110) and an instrument manipulator 130 that controls the attached instrument 120. The entry guide 124 is mounted onto the entry guide manipulator, which includes a robotic positioning system for positioning the distal end of the entry guide 124 at the desired target surgical site. The robotic positioning system may be provided in a variety of forms, such as a serial link arm having multiple degrees of freedom (e.g., six degrees of freedom) or a jointed arm that provides a remote center of motion (due to either hardware or software constraints) and which is positioned by one or more unpowered, lockable setup joints mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator may be coupled to the entry guide manipulator such that the instrument manipulator 130 moves in conjunction with the entry guide 124.

The surgical instrument 120 is detachably connected to the robotic instrument manipulator 130. The robotic manipulator includes a coupler 132 to transfer controller motion from the robotic manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

Figure 3:
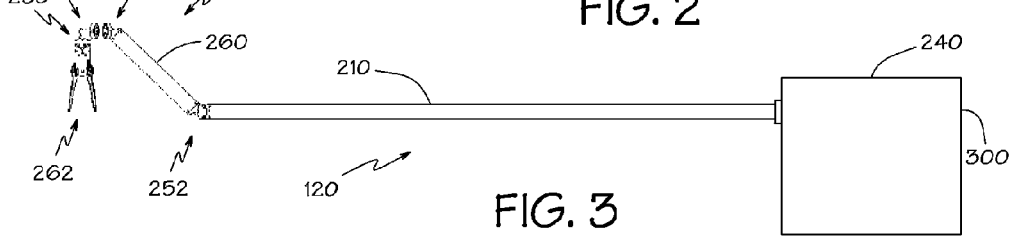
FIG. 3 is a plan view of a surgical instrument for use with a robotic manipulator.

FIG. 3 is a plan view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical devices such as the forceps 262 shown, a needle driver, a cautery device, a cutting tool, an imaging device (e.g., an endoscope or ultrasound probe), or a combined device that includes a combination of two or more various tools and imaging devices.

In the embodiment shown, the surgical tool 262 is coupled to the elongate tube 210 by four joints 252, 254, 256, 258 that allow the position and orientation of the surgical tool to be manipulated. Two of the joints 252, 254, which may be referred to as "joggle" joints, are coupled by a tube 260 and move cooperatively to offset the surgical tool 262 from the axis of the elongate tube 210. The other two joints 256, 258, which may be referred to as "wrist" joints, couple the surgical tool 262 to one of the joggle joints 254 and move cooperatively to control the wrist motion that orients the surgical tool.

Figure 4:
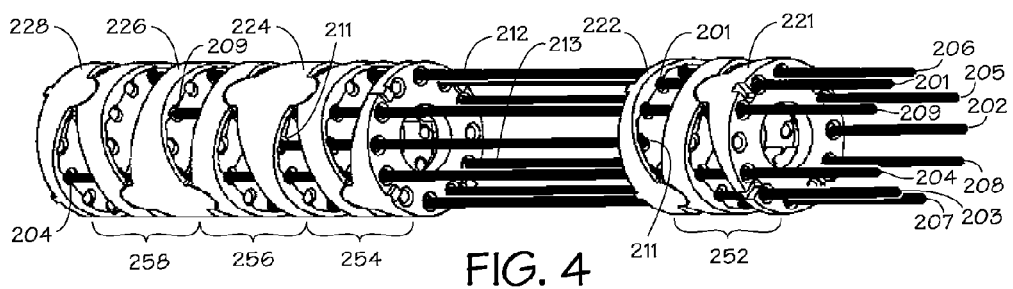
FIG. 4 is a perspective view of an illustrative embodiment of the distal portion of the surgical instrument.

FIG. 4 is a perspective view of an illustrative embodiment of the four joints 252, 254, 256, 258 of the distal portion 250 of the surgical instrument 120. Surgical instruments that are used with the invention are controlled by a plurality of flexible cables. Cables provide a means of transmitting forces to the joints that is compact and flexible. A typical elongate tube 210 for a surgical instrument 120 is small, perhaps six millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale because forces and strengths of materials do not scale at the same rate as the size of the mechanisms. The cables must fit within the elongate tube 210 and be able to bend as they pass through the joints 252, 254 that offset the surgical tool 262.

In the embodiment of the four joints 252, 254, 256, 258 shown, each joint consists of three segments that allow the most distal segment to be positioned with two degrees of angular freedom. The joints 252, 254, 256, 258 have substantially the same diameter as the elongate tube 210. Three cables are coupled to each of the distal segments 222, 224, 226, 228 of the four joints 252, 254, 256, 258 to control the orientation of the distal segments.

A first group of three cables 201, 202, 203 is coupled to the most proximal joint 252. These three cables are coupled to the distal section 222 of the joint. In the embodiment illustrated, the three cables are substantially equally spaced around the circular periphery of the joint 252. In other embodiments, the small diameter of the joint mechanisms may require the cables to be somewhat displaced from the preferred equally spaced positions. A second group of cables 211, 212, 213 is coupled between the two joints 252, 254 that offset the surgical tool 262 from the axis of the elongate tube 210. The three cables of the second group illustrated are located so that the six cables of the first and second groups are substantially equally spaced around the circular periphery of the joint 252 in the embodiment illustrated. The second group of three cables 211, 212, 213 causes the more distal joint 254 to move in response to movements of the more proximal joint 252 such that the distal section 224 of the more distal joint remains substantially parallel to proximal section 221 of the more proximal joint. Thus the first group of three cables 201, 202, 203 provides the control of the two joints 252, 254 that offset the surgical tool 262 from the axis of the elongate tube 210. The parallel motion mechanism of these two joints 252, 254 is more fully described in U.S. Patent Application Publication No. 2008/0065102, which is hereby incorporated by reference in its entirety.

Two joints 256, 258 are used cooperatively to control the wrist motion of the surgical tool 262 to provide a greater range of motion than a single joint provides. A third group of three cables 205, 207, 209 is coupled to the distal section 226 of one of these joints 256 and a group of three cables 204, 206, 208 is coupled to the distal section 228 of the other of these joints 258. The six cables of the third and fourth groups are substantially equally spaced around the circular periphery of the joints in the embodiment illustrated.

Figure 5:
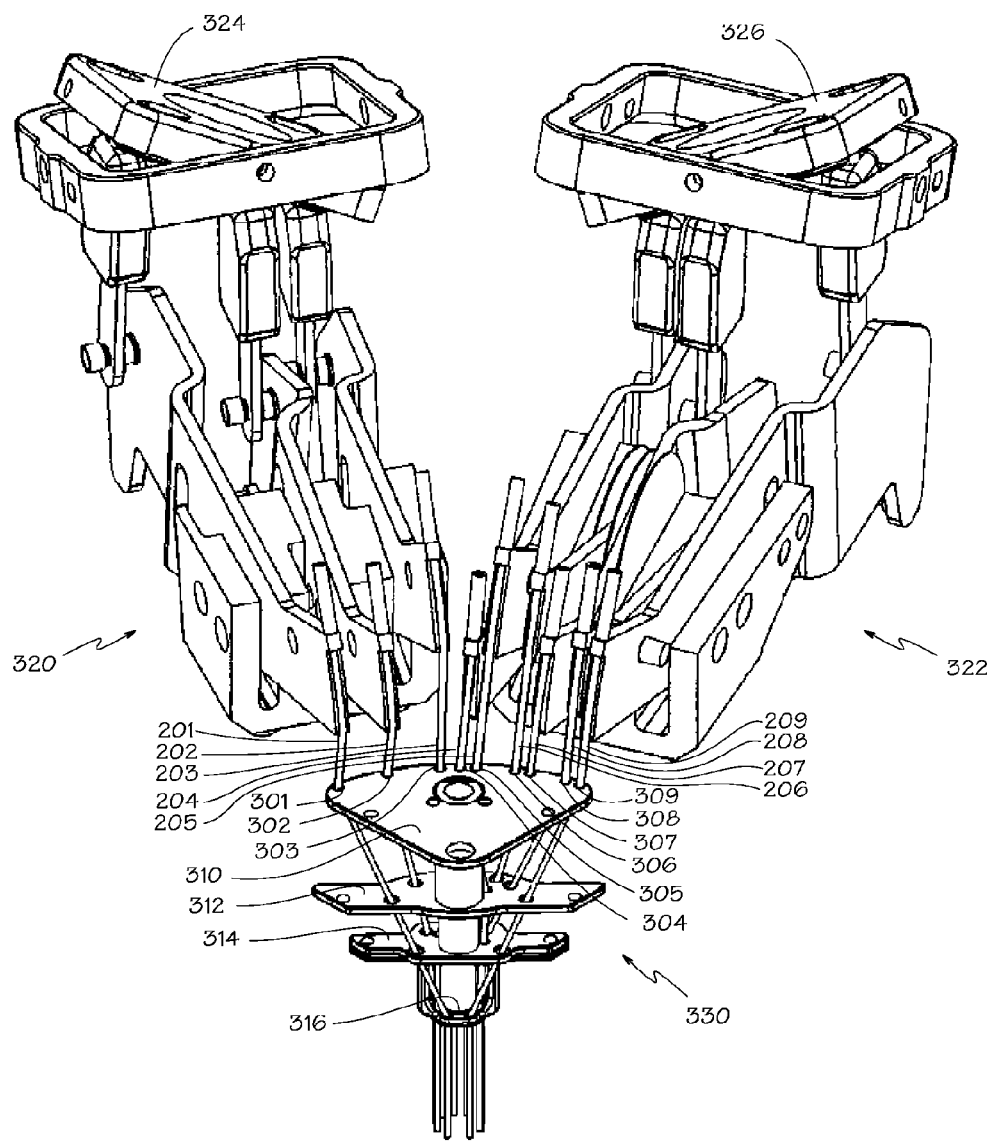
FIG. 5 is a perspective view of an exemplary mechanism for coupling the actuator forces to the cables of the surgical instrument.

FIG. 5 is a perspective view of an exemplary mechanism 320, 322 for coupling the actuator forces to the cables 201-209. It is advantageous to use an actuator mechanism that is substantially larger than the diameter of the elongate tube 210 and the surgical tool 262 and use a coupler mechanism that translates the actuator forces to a more compact arrangement of the cables 201-209. The mechanism 320, 322 illustrated provides two input joint plates 324, 326 that are moved by the actuator in proportion to the desired motion of the joints 252, 254, 256, 258 of the distal portion 250 of the surgical instrument 120.

The left portion 320 of the mechanism illustrated controls the first group of three cables 201, 202, 203. As explained above, this controls the two most proximal joints 252, 254 of the of the surgical instrument 120 which control the offset of the surgical tool 262 from the axis of the elongate tube 210.

The right portion 322 of the mechanism illustrated controls the third group of three cables 205, 207, 209 and the fourth group of three cables 204, 206, 208. As explained above, this the two most distal joints 256, 258 of the of the surgical instrument 120 which controls the orientation of the surgical tool 262. Each cable of the third group is paired with a cable of the fourth group. Each pair of cables is coupled to their respective distal sections 226, 228 at diametrically opposed locations. The cables connected to the most distal section 228 move at twice the rate and in the opposite direction as the paired cable connected to the less distal section 226. This related motion of the paired cables is provided by a mechanical coupling of adjacent lever arms in the right portion 322 of the coupling mechanism.

The mechanical considerations of the coupling mechanism 320, 322 results in the cables having a substantially linear configuration with the first group of cables 201-203 adjacent one another and the second and third groups of cables 204-209 interleaved. The term "substantially linear configuration" is used to indicate that the cables are generally arranged side by side with a first cable 201 and a last cable 209 and the remaining cables 202-208 between them. This is to be contrasted with the substantially circular configuration of the cables within the elongate tube 210.

It will be appreciated that the desired order of the cables 201-209 adjacent the coupling mechanism 320, 322 is substantially different from the order of the cables adjacent the joints 252, 254, 256, 258 of the distal portion 250 of the surgical instrument 120. A cable guide 330 that embodies the present invention provides a means for reordering the cables 201-209 from the arrangement adjacent the coupling mechanism 320, 322 to the arrangement needed adjacent the joints 252, 254, 256, 258 of the surgical instrument 120.

Figure 6:
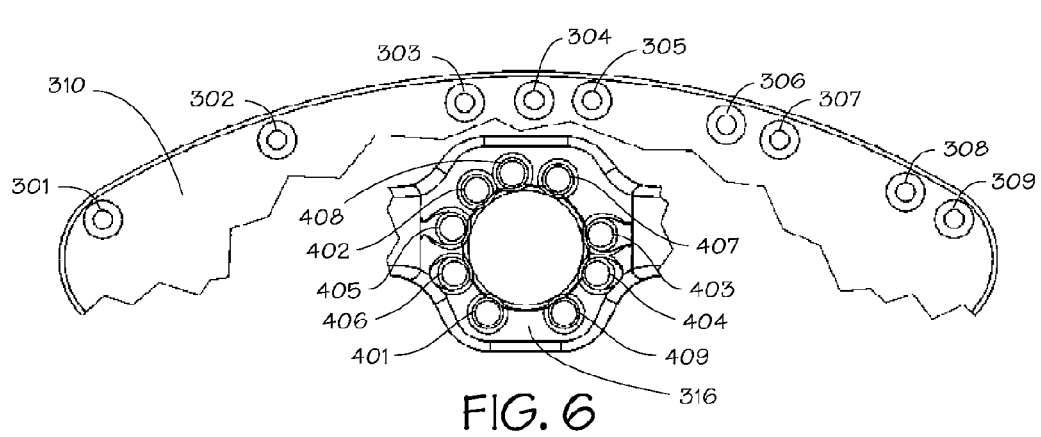
FIG. 6 is a plan view of a portion of the cable guide shown in FIG. 5 with parts broken away.
Figure 7:
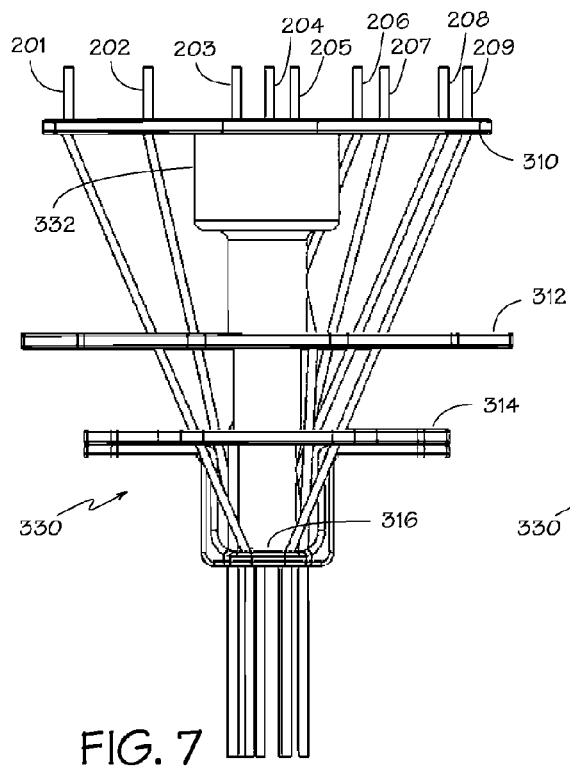
FIG. 7 is a view of the cable guide from a first side.
Figure 8:
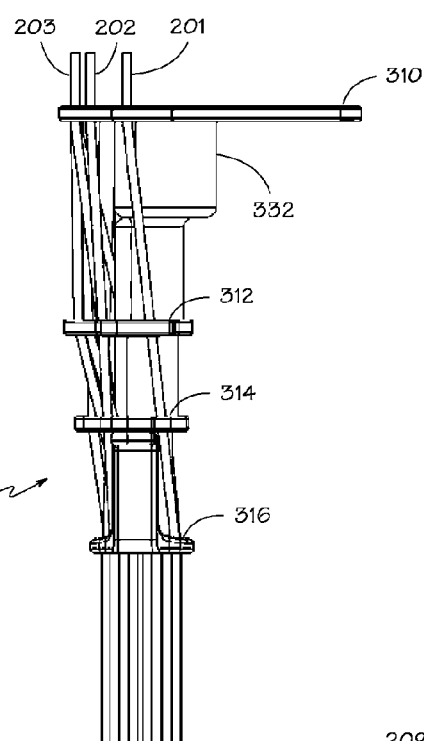
FIG. 8 is a view of the cable guide from a second side.
Figure 9:
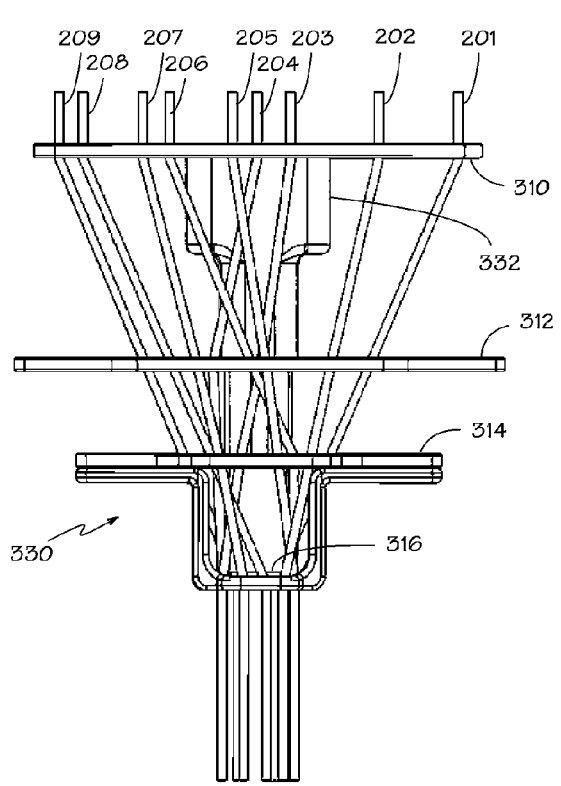
FIG. 9 is a view of the cable guide from a third side.
Figure 10:
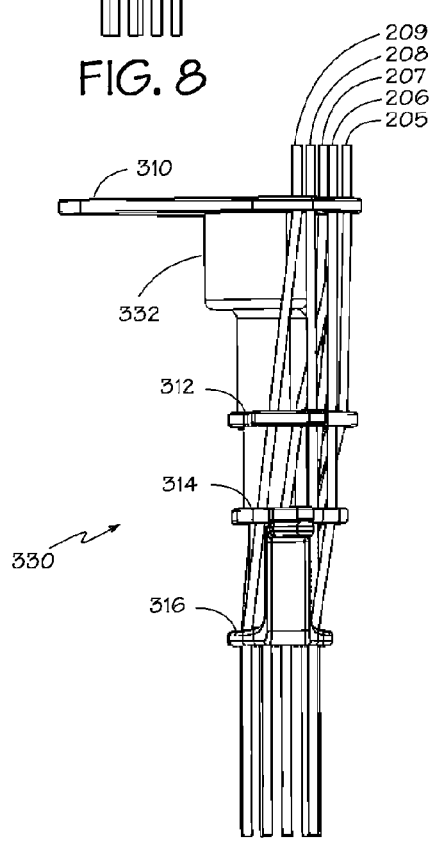
FIG. 10 is a view of the cable guide from a fourth side.

FIG. 6 is a plan view of a portion of the cable guide 330 shown in FIG. 5. The parts shown are broken away so that the cable reordering aspect can be seen clearly.

A first guide plate 310 has a plurality of first guide holes 301-309. The first guide plate 310 is adjacent the coupling mechanism 320, 322. Each of the first guide holes 301-309 receives one of the cables 201-209 in a first order according to the arrangement of the coupling mechanism 320, 322. Each of the first guide holes is identified by a reference numeral that is 100 greater than the reference numeral of the cable that is received by the guide hole.

A second guide plate 316 has a plurality of second guide holes 401-409 equal in number to the plurality of first guide holes 301-309. The second guide plate 316 is adjacent the proximal end of the elongate tube of the surgical instrument 120. Each of the second guide holes 401-409 receives one of the plurality of cables 201-209 in a second order that is different from the first order. The second order is according to the arrangement needed adjacent the joints 252, 254, 256, 258 of the surgical instrument 120. Each of the second guide holes is identified by a reference numeral that is 200 greater than the reference numeral of the cable that is received by the guide hole.

FIG. 6 shows that the first guide holes 301-309 are in a substantially linear arrangement, although slightly curved, while the second guide holes 401-409 are in a substantially circular arrangement. It will be noted that while the second guide holes 401-409 are in the same order as the arrangement needed adjacent the joints 252, 254, 256, 258 of the surgical instrument 120, they are not necessarily spaced as they are adjacent the joints. It will be appreciated that the cables can readily accommodate differences in spacing between the second guide holes 401-409 and the joints 252, 254, 256, 258.

FIG. 6 further shows that the cables are required to cross one another to be reordered between the first and second arrangements. The leftmost three cables 201-203 in the first arrangement are substantially equally spaced in the second arrangement and two other cables are located between each of these three cables. Each adjacent pair of cables of the rightmost six cables 204-209 in the first arrangement are substantially diametrically opposite one another in the second arrangement. It will be appreciated that the reordering between the first and second arrangements leads to complex cable routing between the first 310 and second 316 guide plates. It is desirable to provide this cable routing in a manner that avoids cables rubbing against one another. The cable guide 330 shown in FIG. 5 includes two intermediate guide plates 312, 314 located between the first guide plate 310 and the second guide plate 316 to provide this cable routing.

FIGS. 7-10 show views of the cable guide 330 from four sides. The routing of the cables 201-209 may be seen in these views. It should be noted that some cables change direction at the guide holes in the intermediate guide plates 312, 314. The guide holes are preferably located so the cable segments form fairly shallow, oblique angles due to the direction change at the guide hole to minimize the friction between the cables and the guide holes. The intermediate guide plates shown also include cable passages that allow other cables to pass through the plate without changing direction. Cable passages are preferably large enough that a cable can pass through without touching the guide plate and that small variations in the cable routing due to manufacturing variations can be accommodated.

Figure 15:
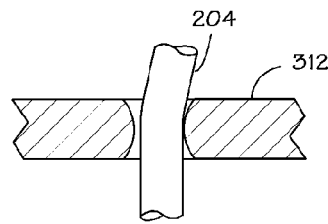
FIG. 15 is a cross section view of a guide hole in the first intermediate guide plate.

FIG. 15 is a cross section view of a guide hole in the first intermediate guide plate 312. The guide holes are preferably rounded as illustrated so that the cable 204 passing through the guide hole is supported over a radius as it changes direction to reduce wear and bending fatigue in the cable. The guide holes are positioned to minimize the "wrap" angle as the cables pass over the radius of the guide hole.

The cable guide illustrated includes a support strut 332 coupled to the first guide plate 310, the intermediate guide plates 312, 314, and the second guide plate 316 to hold the plates in a fixed, spaced apart relationship, as best seen in FIGS. 7-10. The support strut 332 establishes the alignment and spacing of the plates, which is part of establishing the relative positions of the guide holes. In the embodiment illustrated, the support strut 332 has a "stepped" outer surface with increasing diameters to provide shoulder surfaces that the plates rest against. The housing in which the cable guide is installed may provide guide pins and/or additional support so that the guide plates remain fixed with respect to one another.

The support strut 332 shown is coupled to the second guide plate 316 inside the circular arrangement of the guide holes for the cables 201-209. In the embodiment illustrated, the guide holes in the various plates 310, 312, 314, 316 are arranged so that the cables 201-209 do not rub against the support strut 332. In other embodiments, cables may rub against the support strut to further change their direction. The support strut 332 shown is constructed as a tube with a passage through the center that can be used to route mechanisms to the center of the elongate tube 210, such as a flexible driving mechanism to operate a surgical end effector 262 at the distal end of the elongate tube. Routing the actuating mechanism for the end effector 262 along the central axis of the elongate tube 210 is advantageous because the actuating mechanism is then relatively unaffected by the bending of the elongate tube 210, such as the bending at the distal joints 252, 254, 256, 258.

FIGS. 11-14 show views of each of the various plates 310, 312, 314, 316 of the cable guide 330 from the top with the cables 201-209 cut away just below the plate above to allow the details of the exemplary cable routing illustrated to be seen more clearly.

Figure 11:
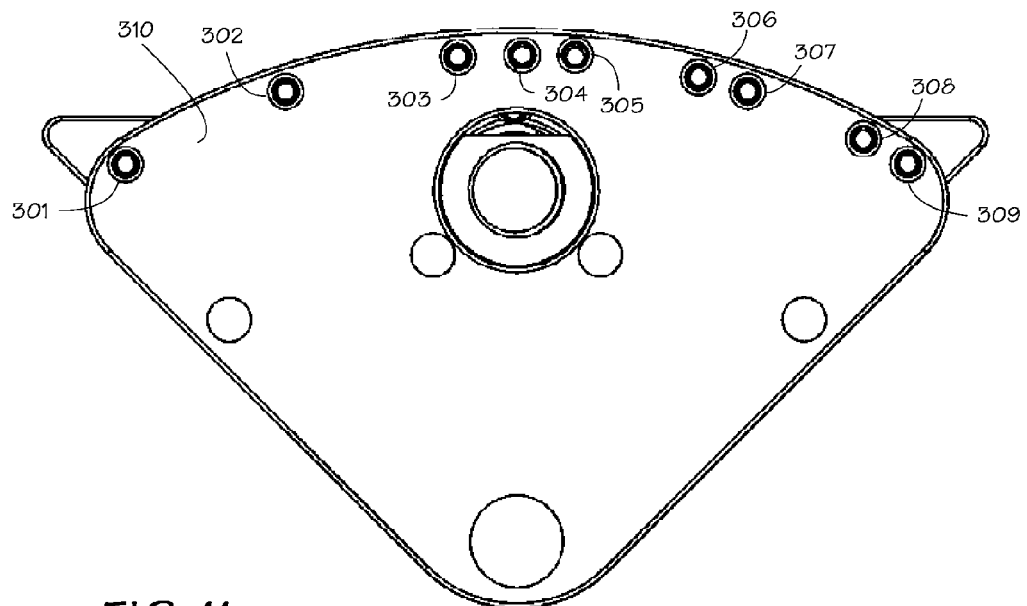
FIG. 11 is a top view of a first guide plate of the cable guide.

FIG. 11 shows a top view of the first guide plate 310. The substantially linear arrangement of the guide holes 301-309 receive the corresponding cables 201-209 from the coupling mechanism 320, 322. The action of the coupling mechanism 320, 322 as actuator forces are applied causes the path of the cables to change. The guide holes 301-309 of the first guide plate 310 redirect the cables as necessary to fix the position of the cables at the first guide plate 310 of the cable guide 330.

Figure 12:
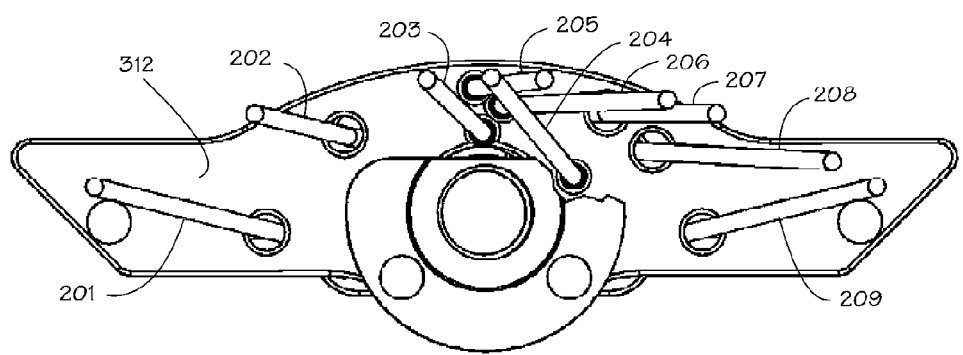
FIG. 12 is a top view of a first intermediate guide plate of the cable guide.

FIG. 12 shows a top view of the first intermediate guide plate 312. Four of the cables 203-206 are redirected by guide holes in the first intermediate guide plate 312. The remaining five cables 201-202, 207-209 pass through cable passages in the first intermediate guide plate 312 without changing direction. The cable passages may aid in installation of the cables by holding the cables in the correct position as the cables are threaded through the cable guide.

Figure 13:
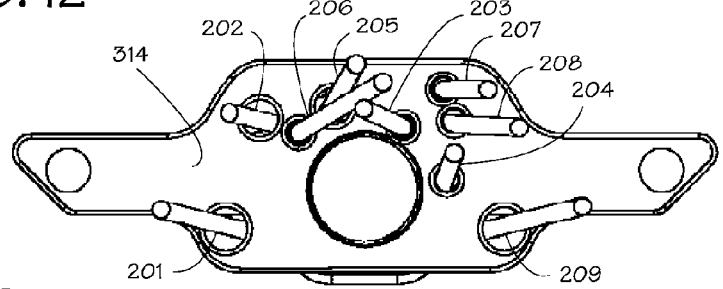
FIG. 13 is a top view of a second intermediate guide plate of the cable guide.

FIG. 13 shows a top view of the second intermediate guide plate 314. Five of the cables 203-204, 206-208 are redirected by guide holes in the second intermediate guide plate 314. The remaining four cables 201-202, 205, 209 pass through cable passages in the second intermediate guide plate 314 without changing direction.

Figure 14:
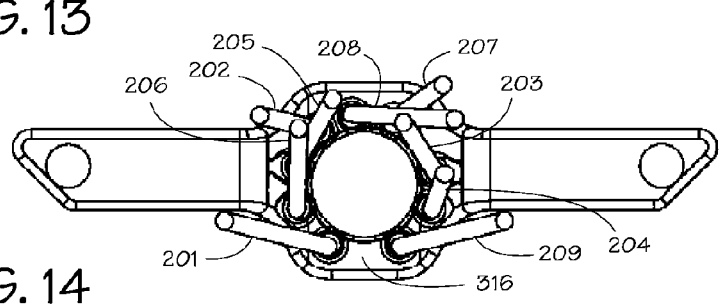
FIG. 14 is a top view of a second guide plate of the cable guide.

FIG. 14 shows a top view of the second guide plate 316. The substantially circular arrangement of the guide holes in the second guide plate 316 receive the cables 201-209 in the order needed for the cable arrangement adjacent the joints 252, 254, 256, 258 of the surgical instrument 120. The cables at the second guide plate 316 are not necessarily spaced as they are adjacent the joints. The diameter of the guide hole arrangement of the second guide plate 316 may be substantially larger than the diameter of the elongate shaft 210. Therefore, all the cables 201-209 change direction at the guide holes in the second guide plate 316 to make the transition to the diameter and spacing of the cable arrangement as it passes through the elongate shaft 210.

Figure 16:
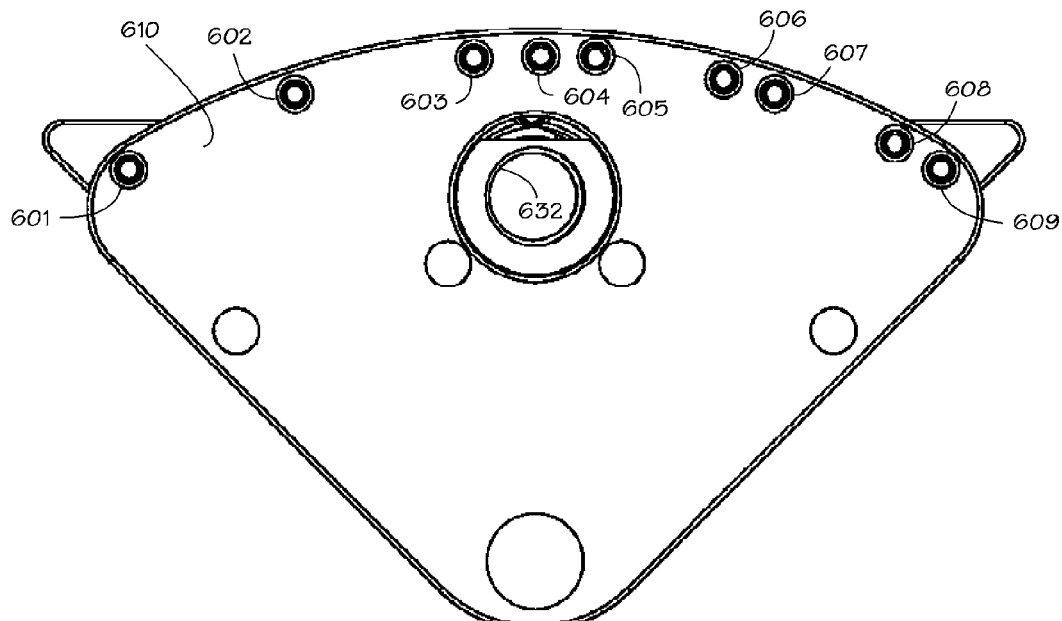
FIG. 16 is a top view of a first guide plate of another embodiment of the cable guide.

FIG. 16 shows a top view of a first guide plate of another embodiment of the cable guide. The first guide plate of this embodiment of the cable guide is substantially identical to the first guide plate 310 of the previous embodiment shown in FIG. 11. The substantially linear arrangement of the guide holes 601-609 receive the corresponding cables 501-509 from the coupling mechanism 320, 322. The action of the coupling mechanism 320, 322 as actuator forces are applied causes the path of the cables to change. The guide holes 601-609 of the first guide plate 610 redirect the cables as necessary to fix the position of the cables at the first guide plate 610 of the cable guide.

Figure 17:
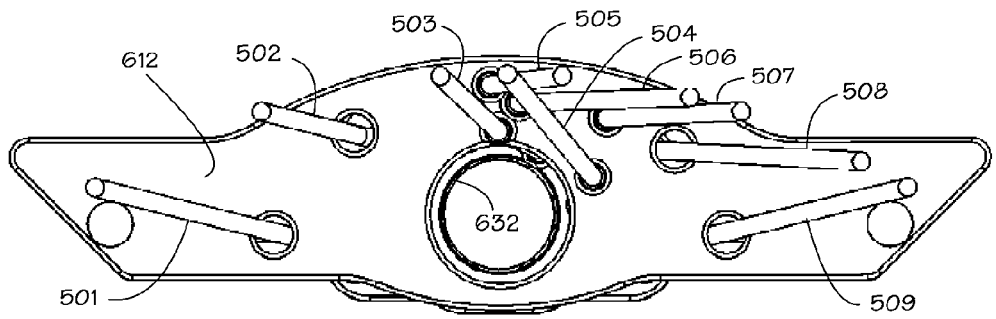
FIG. 17 is a top view of an intermediate guide plate of the embodiment of the cable guide shown in FIG. 16.

FIG. 17 shows a top view of an intermediate guide plate 612 of the embodiment of the cable guide shown in FIG. 16. The intermediate guide plate 612 of this embodiment of the cable guide is similar to the first intermediate guide plate 312 of the previous embodiment shown in FIG. 12. In this embodiment, a cable 507 that was routed through a cable passage in the first intermediate guide plate of the previous embodiment is redirected by a guide hole 617 in the intermediate guide plate 612 of this embodiment.

Figure 18:
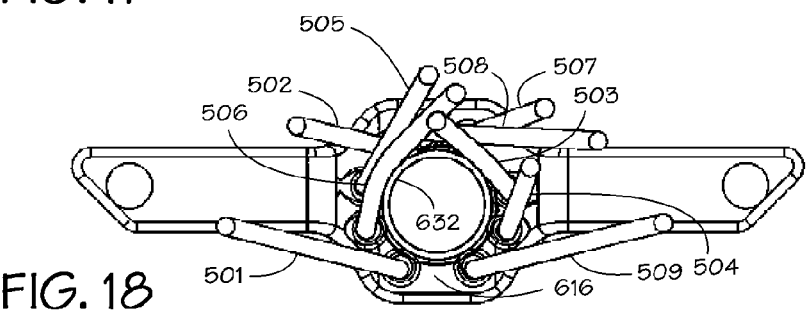
FIG. 18 is a top view of a second guide plate of the embodiment of the cable guide shown in FIG. 16.

FIG. 18 shows a top view of a second guide plate 616 of the embodiment of the cable guide shown in FIG. 16. The second guide plate 616 of this embodiment of the cable guide is substantially identical to the second guide plate 316 of the previous embodiment shown in FIG. 14.

This embodiment of the cable guide includes a support strut 632 coupled to the first guide plate 610, the intermediate guide plate 612 and the second guide plate 616 to hold the plates in a fixed, spaced apart relationship, which is substantially identical to the support strut 332 of the previous embodiment. The support strut 632 establishes the alignment and spacing of the plates, which is part of establishing the relative positions of the guide holes. The support strut 632 shown is coupled to the second guide plate 616 inside the circular arrangement of the guide holes for the cables 501-509. In this embodiment, two cables 203, 206 rub against the support strut 632 to change their direction between the intermediate guide plate 612 and the second guide plate 616.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A cable guide that re-orders a plurality of cables that transmit force to a teleoperated surgical instrument, the cable guide comprising:
a first guide plate that has a plurality of first guide holes, each of the plurality of cables being received through a corresponding one of the first guide holes in a first order as provided by an actuator mechanism that provides a plurality of forces at a proximal end of an elongate tube;
a second guide plate that has a plurality of second guide holes, each of the plurality of cables being received through a corresponding one of the second guide holes in a second order as required to transmit the plurality of forces to a plurality of movable joints at a distal end of the elongate tube, the second guide plate adjacent the proximal end of the elongate tube, the second order different from the first order; and
a first intermediate guide plate located between the first guide plate and the second guide plate, the first intermediate guide plate having one or more first intermediate guide holes, each of the first intermediate guide holes receiving and changing the direction of one cable from the plurality of cables.

2. The cable guide of claim 1 wherein the first intermediate guide plate further includes one or more cable passages, one or more of the plurality of cables being received through a corresponding one or more of the cable passages, the one or more cable passages being located such that each cable passing through the corresponding one or more cable passage does not change direction at the first intermediate guide plate.

3. The cable guide of claim 1 wherein the plurality of first guide holes are in a substantially linear arrangement.

4. The cable guide of claim 1 wherein the plurality of second guide holes are in a substantially circular arrangement.

5. The cable guide of claim 4 wherein two of the plurality of cables are received by adjacent first guide holes and are received by second guide holes that are substantially diametrically opposed.

6. The cable guide of claim 4 further comprising a support strut coupled to the first guide plate, the second guide plate, and the first intermediate guide plate, the support strut being coupled to the second guide plate inside the arrangement of the second guide holes.

7. The cable guide of claim 1 further comprising a second intermediate guide plate located between the first intermediate guide plate and the second guide plate, the second intermediate guide plate having one or more second intermediate guide holes, one or more of the plurality of cables being received through a corresponding one or more of the second intermediate guide holes, the one or more second intermediate guide holes being located such that each cable passing through the corresponding one or more second intermediate guide holes changes direction at the second intermediate guide plate.

8. The cable guide of claim 7 wherein the second intermediate guide plate further includes one or more cable passages, one or more of the plurality of cables being received through a corresponding one or more of the cable passages, the one or more cable passages being located such that each cable passing through the corresponding one or more cable passage does not change direction at the second intermediate guide plate.

9. The cable guide of claim 7 further comprising a support strut coupled to the first guide plate, the second guide plate, the first intermediate guide plate, and the second intermediate guide plate, the plurality of second guide holes being in a substantially circular arrangement, and the support strut being coupled to the second guide plate inside the arrangement of the second guide holes.

10. The cable guide of claim 9 wherein the support strut is arranged such that at least one cable of the plurality of cables is redirected by the support strut.

11. A force transmission for a teleoperated surgical instrument comprising:
a plurality of movable joints in the teleoperated surgical instrument at a distal end of an elongate tube;
an actuator mechanism to provide a plurality of forces at a proximal end of the elongate tube;
a plurality of cables, each of the plurality of cables coupled at a first end to the actuator mechanism and at an opposite second end to one of the plurality of movable joints in the teleoperated surgical instrument, the plurality of cables passing through the elongate tube in a second order as required by the plurality of movable joints and transmitting the plurality of forces from the actuator mechanism to the plurality of movable joints;
a first guide plate located between the actuator mechanism and the proximal end of the elongate tube, the first guide plate having a plurality of first guide holes through which the plurality of cables pass, each of the first guide holes to receive one of the plurality of cables in a first order as provided by the actuator mechanism;
a second guide plate located between the first guide plate and the proximal end of the elongate tube, the second guide plate having a plurality of second guide holes through which the plurality of cables pass, the plurality of second guide holes being equal in number to the plurality of first guide holes, each of the second guide holes to receive one of the plurality of cables in the second order as required by the plurality of movable joints, the second order different from the first order; and
a first intermediate guide plate located between the first guide plate and the second guide plate, the first intermediate guide plate having a plurality of first intermediate guide holes, each of the first intermediate guide holes to receive and change the direction of one of the plurality of cables.

12. The force transmission of claim 11 wherein the first intermediate guide plate further includes one or more cable passages, each of the cable passages to receive one of the plurality of cables and located such that a cable passing through the cable passage does not change direction at the first intermediate guide plate.

13. The force transmission of claim 11 wherein the plurality of second guide holes are in a substantially circular arrangement and two of the plurality of cables are received by adjacent first guide holes and are received by second guide holes that are substantially diametrically opposed.

14. The force transmission of claim 11 further comprising a second intermediate guide plate located between the first intermediate guide plate and the second guide plate, the second intermediate guide plate having one or more intermediate guide holes and one or more cable passages, the second intermediate guide holes to receive one of the plurality of cables and located such that a cable passing through the second intermediate guide hole changes direction at the second intermediate guide plate, the cable passages to receive one of the plurality of cables and located such that each cable passing through the cable passage does not change direction at the second intermediate guide plate.

15. The force transmission of claim 14 further comprising a support strut coupled to the first guide plate, the second guide plate, the first intermediate guide plate, and the second intermediate guide plate, the plurality of second guide holes being in a substantially circular arrangement, and the support strut being coupled to the second guide plate inside the circular arrangement of the second guide holes.

16. The force transmission of claim 15 wherein the support strut is arranged such that at least one cable is redirected by the support strut.

17. A teleoperated surgical instrument comprising:
an elongate tube;
a first distal end component and a second distal end component at a distal end of the elongate tube, the first distal end component associated with a first joint and the second distal end component associated with a second joint;
an actuator mechanism to provide a first force and a second force at a proximal end of the elongate tube;
a first cable passing through the elongate tube to transmit the first force from the actuator mechanism to the first distal end component;
a second cable passing through the elongate tube to transmit the second force from the actuator mechanism to the second distal end component;
a first guide plate located adjacent the proximal end of the elongate tube, the first guide plate having a first guide hole and a second guide hole, wherein the first cable is received through the first guide hole and the second cable is received through the second guide hole in a first order determined by the actuator mechanism;
a second guide plate located between the first guide plate and the proximal end of the elongate tube, the second guide plate having a third guide hole and a fourth guide hole, wherein the first cable is received through the third guide hole and the second cable is received through the fourth guide hole in a second order different from the first order, the second order determined by the first distal end component and the second distal end component; and
an intermediate guide plate located between the first guide plate and the second guide plate, wherein the intermediate guide plate has an intermediate guide hole, the first cable is received through and changes direction at the intermediate guide hole.

18. The surgical instrument of claim 17:
wherein the intermediate guide plate includes a cable passage, the second cable is received through the cable passage, and the second cable does not change direction at the intermediate guide plate.

19. The surgical instrument of claim 17:
wherein the first guide hole and the second guide hole are adjacent one another, and the third guide hole and the fourth guide hole are substantially diametrically opposed in a substantially circular pattern of guide holes in the second guide plate.

20. The surgical instrument of claim 17 further comprising:
a second intermediate guide plate located between the intermediate guide plate and the second guide plate, wherein the second intermediate guide plate has a second intermediate guide hole and a third intermediate guide hole, the first cable is received through the second intermediate guide hole, and the second cable is received through the third intermediate guide hole.

21. The surgical instrument of claim 20:
wherein the second intermediate guide hole is positioned to change the direction of the first cable at the second intermediate guide plate.

22. The surgical instrument of claim 20:
wherein the third intermediate guide hole is positioned to change the direction of the second cable at the second intermediate guide plate.

23. The surgical instrument of claim 17 further comprising:
a second intermediate guide plate located between the intermediate guide plate and the second guide plate;

wherein the second intermediate guide plate includes a cable passage, the first cable is received through the cable passage, and the first cable does not change direction at the second intermediate guide plate.

24. The surgical instrument of claim 17 further comprising:
a second intermediate guide plate located between the intermediate guide plate and the second guide plate;
wherein the second intermediate guide plate includes a cable passage, the second cable is received through the cable passage, and the second cable does not change direction at the second intermediate guide plate.

* * * * *